United States Patent [19]

Wristers

[11] 4,098,833
[45] Jul. 4, 1978

[54] REGENERATION OF HYDROCARBON CONVERSION CATALYSTS

[75] Inventor: Jos Wristers, Baton Rouge, La.

[73] Assignee: Exxon Research & Engineering Co., Linden, N.J.

[21] Appl. No.: 739,303

[22] Filed: Nov. 5, 1976

Related U.S. Application Data

[63] Continuation-in-part of Ser. No. 577,351, May 14, 1975, Pat. No. 4,025,459.

[51] Int. Cl.² .............. C07C 5/24; C07C 3/50; B01D 15/06
[52] U.S. Cl. .............. 260/666 P; 260/666 R; 260/668 B; 260/683.68; 260/683.7; 260/683.75; 260/671 R; 260/683.51; 252/411 R
[58] Field of Search ........... 260/666 P, 666 R, 683.68, 260/683.7, 683.75, 671, 668 B, 683.51; 252/411

[56] References Cited

U.S. PATENT DOCUMENTS

| | | | |
|---|---|---|---|
| 3,558,514 | 1/1971 | Schutt | 252/411 |
| 3,590,007 | 7/1971 | Schutt | 252/411 |
| 3,852,184 | 12/1974 | Siskin et al. | 260/666 P |
| 3,948,761 | 4/1976 | Siskin et al. | 260/666 P |
| 3,975,299 | 8/1976 | Crathorne et al. | 260/683.68 |
| 4,025,459 | 5/1977 | Wristers | 252/411 |
| 4,036,737 | 7/1977 | Wristers et al. | 252/411 |
| 4,036,738 | 7/1977 | Wristers | 252/411 |

OTHER PUBLICATIONS

George A. Olah et al. *Carbonium Ions* vol. II, pp. 783, 802, 803, Wiley, Intersciences, 1970.

*Primary Examiner*—Veronica O'Keefe
*Attorney, Agent, or Firm*—John W. Ditsler

[57] ABSTRACT

Hydrocarbon conversion catalysts comprising a metal halide in combination with a Bronsted acid containing fluorine that have become deactivated or partially deactivated by the formation of allyl and alkylaromatic carbonium ion complexes with the acid during contact with a hydrocarbon feedstock may be regenerated by contacting said catalyst, in the presence of molecular hydrogen and under suitable regeneration conditions, with a noble metal hydrogenation component. A preferred catalyst comprises tantalum pentafluoride and hydrogen fluoride. Palladium is the preferred noble metal hydrogenation component.

26 Claims, 1 Drawing Figure

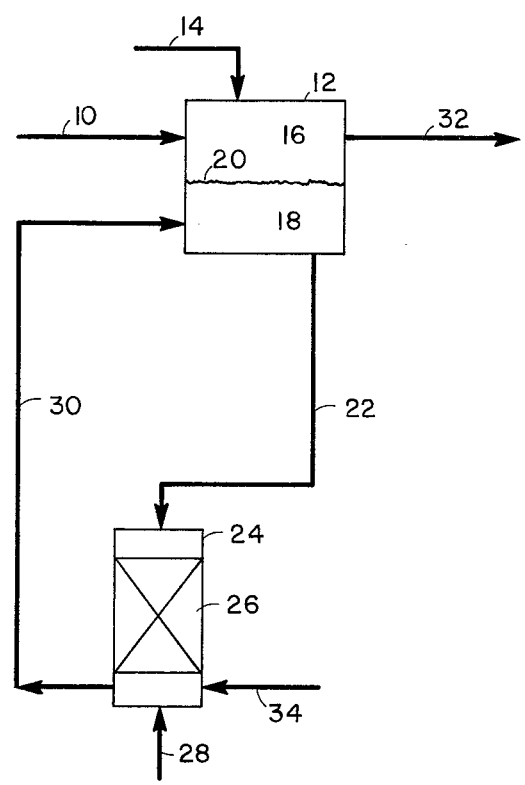

4,098,833

REGENERATION OF HYDROCARBON CONVERSION CATALYSTS

CROSS REFERENCE TO RELATED APPLICATIONS

This application is a continuation-in-part of copending U.S. patent application Ser. No. 577,351 filed May 14, 1975, now U.S. Pat. No. 4,025,459.

BACKGROUND OF THE INVENTION

1. Field of the Invention

The present invention relates to a process for regenerating a catalyst of the type employed in hydrocarbon conversion reactions. More particularly, the present invention relates to a process for regenerating a catalyst comprising a metal halide and a Bronsted acid containing fluorine in the presence of hydrogen and a noble metal hydrogenation component, said catalyst having become deactivated or partially deactivated by contact with hydrocarbons.

2. Description of the Prior Art

It is well known that the activity of Friedel-Crafts type hydrocarbon conversion catalysts declines gradually due to the accumulation of various organic and inorganic contaminants or poisons (such as compounds of carbon, sulfur, nitrogen, oxygen, metals, water and the like) until the catalyst ceases to exhibit an economic activity. In such cases, depending upon various economic factors, the catalyst may be replaced or regenerated to restore desired activity levels.

Several methods have been suggested in the prior art for regenerating supported Friedel-Crafts type hydrocarbon conversion catalysts with a noble metal hydrogenation component (see for example U.S. Pat. Nos. 3,389,191; 3,558,514; 3,590,007 and 3,893,942). It has also been suggested to recover active catalytic material from an aluminum halide/hydrocarbon sludge formed during the conversion of hydrocarbons in the presence of an aluminum halide catalyst (see for example U.S. Pat. Nos. 3,210,292 and 3,227,776). However, none of the foregoing prior art is believed to suggest regenerating the present substantially liquid phase hydrocarbon conversion catalyst with a noble metal hydrogenation component hydrogen.

SUMMARY OF THE INVENTION

Now according to the present invention, it has been discovered that a hydrocarbon conversion catalyst comprising a metal halide in combination with a Bronsted acid containing fluorine, that has become deactivated or partially deactivated by the formation of allyl and alkylaromatic carbonium ion complexes with the acid during contact with a hydrocarbon feedstock, may be regenerated by contacting said catalyst with supported noble metal hydrogenation component in the presence of molecular hydrogen. A preferred catalyst comprises tantalum pentafluoride, niobium pentafluoride a mixtures thereof in combination with hydrogen fluoride. Palladium is a preferred noble metal hydrogenation component.

BRIEF DESCRIPTION OF THE DRAWING

The single FIGURE is a simplified flow diagram of one embodiment of the present invention.

DETAILED DESCRIPTION OF THE INVENTION

The hydrocarbon conversion catalyst system regenerated according to the present invention is composed of a metal halide in combination with a Bronsted acid containing fluorine. Useful metal halide constituents include the fluorides, chlorides and bromides of tantalum, niobium, antimony and boron and the chlorides and bromides of aluminum and gallium. The preferred metal halide catalyst constituents are tantalum, niobium and boron halides, more preferably tantalum and niobium halides. Preferred halides are tantalum pentafluoride, niobium pentafluoride, boron trifluoride and mixtures thereof. More preferred metal halides are tantalum pentafluoride, niobium pentafluoride and mixtures thereof.

The Bronsted acid component of the catalyst system should be a fluoride-containing compound capable of donating a proton to the system, i.e., a protonic acid. Useful acids include hydrogen fluoride, fluorosulfonic acid, trifluoromethanesulfonic acid, and trifluoroacetic acid. The acids may be employed alone or mixed with their corresponding anhydrides. Hydrogen fluoride is normally preferred.

The effectiveness of the catalyst system described herein for hydrocarbon conversion reactions is related to the molar ratio of Bronsted acid to metal halide catalyst constituents. The catalyst should be prepared such that at least an equal molar amount of Bronsted acid relative to metal halide is present in the reaction zone. Desirably, the Bronsted acid/metal halide ratio is at least 2:1, preferably at least about 5:1. In the case of catalyst systems based on tantalum pentafluoride and niobium pentafluoride, the presence of large (5:1 to about 20:1) molar excesses of Bronsted acid in the reaction zone has been found to materially improve reaction rates in the presence of poisons. Depending upon the relative amounts of catalyst constituents used, the catalyst may be a homogeneous solution of Bronsted acid and metal halide or a mixture of solid and dissolved metal halide in Bronsted acid. However, while maintaining at least an equal molar amount of Bronsted acid to metal halide is important to the effectiveness of the hydrocarbon conversion process, such is not the case in the present regeneration process.

In general, the deactivated or partially deactivated hydrocarbon conversion catalyst to be regenerated according to the present invention may be derived from those reactions and side reactions that occur under the influence of Friedel-Craft's catalysts, e.g. isomerization, alkylation, polymerization, cracking, hydrogenation, disproportionation, aromatic isomerization (e.g. ortho- to meta- xylene) and the like (see for example U.S. Pat. Nos. 2,683,763; 2,683,764; 3,708,553; 3,728,411; 3,852,184; 3,888,937; 3,901,790; 3,948,761, the disclosures of which are incorporated herein by reference). Typically, the feedstocks used in such processes will contain hydrocarbons containing from 1 to about 15 carbon atoms, preferably from 1 to about 10 carbon atoms, and will have a 50 percent boiling point below 450° F, preferably below 400° F. However, the present process may also be employed to regenerate catalysts obtained from hydrocarbon conversion processes wherein heavier, i.e., higher boiling, feedstock are employed. Thus, the present process can be conveniently employed to regenerate the catalysts obtained from a variety of hydrocarbon conversion processes and reactions.

The present invention is particularly applicable to regenerating catalysts obtained from isomerization and alkylation reactions. Typical isomerizable feedstocks include acyclic and alicyclic aliphatic hydrocarbons having at least four carbon atoms that are converted to a product enriched in an isomer thereof. Typically, acyclic hydrocarbons having at least four carbon atoms, that is straight chain or branched chain paraffins having from about 4 to 10 carbon atoms, preferably from about 4 to 8 carbon atoms, are converted to branched materials having higher octane ratings. Additionally, alicyclic hydrocarbons (naphthenes) having at least 6 carbon atoms, typically from 6 to about 50 carbon atoms, preferably 6 to 15 carbon atoms, can be converted to isomers thereof by contacting the same with hydrogen in the presence of the catalyst system described previously. Mixtures of acyclic and alicyclic hydrocarbons can be used as the process feedstock. In a typical commercial operation, a paraffin stream containing mixtures of various types of open chain and closed chain paraffins is used as the process feedstock. Typical isomerization reaction conditions are summarized below.

| Range | Suitable | Preferred |
|---|---|---|
| Temperature, °C | 0 –150 | 30 –75 |
| Hydrogen Partial Pressure, atm. | 0.1 –140 | 0.3 –25 |
| Reaction Time, min | 0.5 –1500 | 1 –500 |
| Moles H$_2$/Mole Hydrocarbon | 0.01 –2.5 | 0.1 –1.0 |
| Space Velocity V/Hr./V | 0.05 –200 | 0.25 –50 |

In the alkylation of hydrocarbons with olefins, suitable olefinic starting materials are ethylene, propylene, butylenes, trimethyl ethylene and other isomeric pentenes, and similar higher monoolefinic hydrocarbons of either a straight chain or branched chain structure. Olefins containing 2 to about 12 carbon atoms per molecule are preferred while olefins containing 2 to 5 carbon atoms per molecule are particularly preferred. The reaction mixtures may also contain some amounts of diolefins. Although it is desirable from an economic viewpoint to use the normally gaseous olefins as reactants, normally liquid olefins may also be used. Thus, polymers, copolymers, interpolymers, crosspolymers, etc., of the above-mentioned olefins, as for example, propylene dimer, the diisobutylene and triisobutylene polymers, the codimer of normal and isobutylenes and the like may be used. The use of mixtures of two or more of the above-described olefins is also envisioned for this purpose.

Hydrocarbon feedstocks that are suitable for use in alkylation processes include paraffins, aromatics alkyl substituted aromatic hydrocarbons and mixtures thereof. The paraffins as herein defined include the aliphatic and alicyclic hydrocarbons. The aliphatic hydrocarbons (straight and branched chain materials) contain at least 1, preferably 1 to about 12 carbon atoms per molecule, and may be exemplified by methane, ethane, propane, butanes, methylbutanes, n-pentane, methylpentanes, methylhexanes, and the like. The alicyclic hydrocarbons (naphthenes) contain at least 5, typically from 5 to about 15 carbon atoms per molecule, preferably 6 to 12 carbon atoms and may be exemplified by methylcyclopentane, dimethylcyclopentane, methylcyclohexane, ethylcyclohexane, n-pentylcyclohexane and the like. Useful aromatic and alkylaromatic hydrocarbons contain at least 6, preferably 6 to about 20 carbon atoms per molecule and are exemplified by benzene, ethylbenzene, n-butylbenzene and the like. Other aliphatic or alicyclic hydrocarbons commonly found in conventional petroleum hydrocarbon light naphtha streams and the like may be present. Typical alkylation reaction conditions are summarized below.

| Range | Suitable | Preferred |
|---|---|---|
| Temperature, °C | −100 − +150 | −10 − +80 |
| Hydrogen Partial Pressure, atm. | 0 − 100 | 0 − 25 |
| Reaction Time, Min. | 0.001 −60+ | 0.001 − 45 |
| Space Velocity based on olefin, V/Hr./V | 0.01 − 10 | 0.04 −5 |

As the hydrocarbon conversion reaction proceeds the activity of the catalyst system will decline. Some portions of said system may be deactivated so as to possess essentially no activity to catalyze the hydrocarbon conversion reaction while other portions may be only partially deactivated. While not wishing to be bound by any particular theory, it is believed that the present hydrocarbon conversion catalyst is deactivated or neutralized by contaminants which may be present in the hydrocarbon feedstock or which may be formed in situ during the hydrocarbon conversion reaction. The contaminants form complexes with the metal halide and/or Bronsted acid components of the catalyst system. The complexes are more stable, less acidic, i.e., more basic and less catalytically active, than the Bronsted acid/metal halide complexes of the catalyst system. The complexes formed with the contaminants are substantially insoluble in the hydrocarbon phase and thus accumulate in the catalyst phase. As the complexes accumulate, the acidity of the catalyst is diminished, thereby decreasing the reactivity of the catalyst system. Both organic and inorganic contaminants can cause reduced activity of the present hydrocarbon conversion catalyst. Examples of inorganic materials that can cause the reduced activity are water, which may enter the reaction zone of the hydrocarbon conversion process in the feedstock or as the result of an operational mishap, and metal compounds which result from corrosion of the reaction zone internals or are present in heavier feedstocks, sulfur, nitrogen and oxygen-containing compounds present in the feedstock and the like. Examples of organic materials that can cause reduced activity are stable unsaturated ions, e.g. allylic and/or alkylaromatic carbocations formed in situ during the hydrocarbon conversion reaction. By allylic carbocations are meant materials of the form

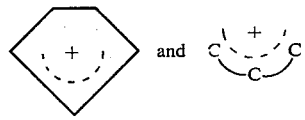

respectively, which are ultimately formed after a number of reactions from hydrocarbons such as hexanes, cyclohexanes, heptanes, etc. By alkylaromatic carbocations are meant materials of the form

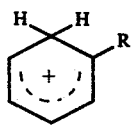

which are formed from alkylaromatics such as ethyl benzene, xylenes, toluene and the like, R being an alkyl or alkylaromatic compound. It should be clearly understood that the present invention is suitable for regenerating at least a portion of a catalyst that has become deactivated by contact with organic, i.e., hydrocarbon, contaminants (not inorganic, i.e., non-hydrocarbon, contaminants) such that allylic and/or alkylaromatic carbocations will be present in said catalyst. Thus, in order to obtain maximum catalyst activity and catalyst life, it is desirable that substantially all of the aforementioned inorganic contaminants be removed from the feedstock, from any diluents and from individual catalyst constituents prior to use in the hydrocarbon conversion process. By substantially is meant that the mole ratio of contaminants to metal halide is less than 1:2, preferably less than 1:4, and more preferably less than 1:5.

The level of activity at which the catalyst should be regenerated is not only a matter of ability to catalyze the reaction, but also a matter of economics. For example, it may be desirable to regenerate a mildly deactivated catalyst to essentially fresh catalyst activity rather than allow the catalyst to be reduced to a much lower level of activity and be regenerated to fresh or to less than fresh activity. As used herein, the term "regeneration" or "regenerated" means recovering a catalyst that possesses a greater activity for hydrocarbon conversion than that possessed by the deactivated or partially deactivated catalyst. It should be understood that the regeneration process of the present invention is applicable to catalysts such as those defined above which have lost some degree of activity and that the regeneration may only partially restore the lost activity.

In the process of the present invention, the deactivated or partially deactivated hydrocarbon conversion catalyst described herein is regenerated by contact with a noble metal hydrogenation component and hydrogen. The noble metal hydrogenation component may be employed alone, i.e., unsupported as a metal black, or in conjunction with other materials to hydrogenate unsaturated hydrocarbons. The noble metal can be of the platinum group (platinum, palladium, iridium) or the palladium group (palladium, ruthenium, rhodium). Of these, platinum, palladium and iridium are preferred, palladium and platinum more preferred with palladium being most preferred. If sulfur or sulfur compounds is present in the hydrocarbon feedstock, platinum and iridium are preferred, platinum being most preferred. It is desirable that sulfur compounds be removed from the system prior to regeneration.

The hydrogenation component may be incorporated on a suitable solid carrier or support. Any support which does not react with the acidic components of the catalyst system under regeneration conditions may be used. Although the support will be employed preferably in a fixed bed process, the support should be capable of mixing with the acidic components; that is, the hydrogenation component may exist, likely as a slurry or dispersion, in the acid catalyst. In such situations, the supported noble metal can be separated from said catalyst by filtration, centrifugation or other conventional solid-liquid separation methods. Supports that can be used are charcoal, char, carbon, coke, fluorided or sulfonated refractory oxides, Teflon and the like. Supports such as alumina, silica, titania and other of these refractory oxides are, in general, not suitable due to the susceptibility of these materials to attack and degradation by fluorides. However, such reactive supports may be rendered inert and, thus, usable by coating them with an inert material such as antimony trifluoride or aluminum trifluoride. Carbon is a preferred support material.

The supported hydrogenation component of the catalyst system is generally commercially available but can easily be prepared by contacting the carbon support with an aqueous solution of the metal halide, removing the water by evaporation and then reducing with hydrogen for 2 hours at about 300° C. Although particle size is not a critical item of the make-up of the catalyst, the hydrogenation component may range preferably in particle diameter size from 38 micrometers to 25 millimeters, preferably 75 micrometers to 12.5 millimeters.

The amount of hydrogenation component utilized is not critical but should be sufficient to regenerate; i.e., to effect an increase in the activity, the hydrocarbon conversion catalyst. The concentration of the noble metal on the support can range from about 0.01 to about 50 wt.%, preferably from about 0.05 to about 20 wt.%, more preferably about 0.1 to about 10 wt.% and most preferably from about 0.1 to about 5 wt.% based on the support. Activity begins to be increased when the hydrogenation component is present in only catalytic amounts; i.e., at least about 0.0001 wt.% metal hydrogenation component, preferably 0.0001 wt.% and more preferably at least about 0.05 wt.% based on acid. Increasing amounts of hydrogenation component serve to simply increase the regeneration rate. Thus, minute amounts may be employed.

The amount of hydrogen present during regeneration is not critical provided there is an amount sufficient to maintain a hydrogen partial pressure of at least 5 psig and the hydrogen is substantially dispersed in the catalyst phase. The hydrogen may be derived from any suitable source. Typically, in a refinery operation, the hydrogen employed may be a crude or an impure hydrogen stream such as that obtained from a naphtha reforming operation. The hydrogen may be introduced into the regeneration zone alone or be mixed with the deactivated or partially deactivated catalyst prior to introduction into the zone. The present regeneration process is exothermic and, as such, should be effected under conditions that will promote favorable temperature control.

In general, the temperature at which the present regeneration process is effected may range broadly. Typically, the temperature will range from about 0° to about 150° C, preferably from about 0° to about 100° C, more preferably from about 0° to about 90° C. Most preferably the regeneration is effected at a temperature ranging from about 25° to about 70° C.

The total pressure at which the regeneration is effected is not critical and will depend upon the extent of catalyst deactivation which, in turn, will depend upon the nature of the material being processed, as well as other process variables. The regeneration process is preferably conducted at conditions sufficient to maintain the hydrocarbon conversion catalyst substantially in the liquid phase. Hydrogen partial pressures during regeneration may vary widely, but as noted above, should be at least about 5 psig. Preferably, the hydrogen partial pressure should range from about 5 to about 2000 psig, more preferably from about 10 to about 1000 psig and still more preferably from about 25 to about 300 psig.

The contact time required need only be that sufficient to obtain a regenerated catalyst that possesses a greater activity for hydrocarbon conversion than that possessed by said deactivated or partially deactivated hydrocarbon conversion catalyst. Thus, the contact time may vary from a few seconds to several hours depending on the temperature, the components of the catalyst, and other interrelated variables. In general, the contact time will vary from 1 second to about 100 hours, preferably from 10 seconds to about 50 hours, more preferably from about 30 seconds to about 5 hours and most preferably from 1 minute to 30 minutes.

The deactivated or partially deactivated catalyst may be regenerated in any suitable apparatus. Contacting may be effected in batch, multiple batch, semicontinuous, or continuous operation. For example, it may be carried out in continuous contacting equipment such as simple gravity operated contactors with no mechanical agitator, mechanically agitated contactors, centrifugal contactors, or packed or unpacked towers employing countercurrent or concurrent techniques with or without mixing orifices. The contacting equipment should be of appropriate design to insure intimate contact between the catalyst, which is at least partially deactivated, and the hydrogen. Preferably, a high efficiency multi-stage contactor will be used. Equipment most suitable for a specific application can be selected by one skilled in the art. The contacting equipment does not require the use of any special materials of construction at temperatures less than 70° C, i.e., carbon steel and Teflon are quite satisfactory. However, at temperatures of at least 70° C, alloy materials such as Carpenter 20 Cb-3 steel (Alloy 20), monel, Hastelloy C, aluminum 5052, aluminum 6061, and the like may be required.

The present invention may be more clearly understood by the description below and by reference to the accompanying FIGURE. Such details are included as are necessary for a clear understanding of how the present invention operates. No intention is made to unduly limit the scope of the present invention to the particular configuration shown as other configurations are contemplated. Various items such as valves, pumps, steam lines, instrumentation, and other process equipment and control means have been omitted therefrom for the sake of simplicity. Variations obvious to those having ordinary skill in the art of catalyst regeneration processes are included within the broad scope of the present invention.

Referring now to the Figure, there is illustrated the present regeneration process integrated with a hydrocarbon conversion process, e.g. an isomerization process. A feedstock containing, for example, isomerizable hydrocarbons is shown being introduced via line 10 into isomerization process 12. Preferably, the feedstock is purified of inorganic contaminants such as sulfur, nitrogen, and oxygen-containing compounds prior to being introduced into isomerization process 12. A suitable method for effecting said purification is disclosed in U.S. Pat. No. 3,957,628, the disclosures of which are incorporated herein by reference. In isomerization zone 12, the feedstock is contacted under isomerization conditions with a preferred isomerization catalyst comprising tantalum pentafluoride in combination with at least a molar equivalent of hydrogen fluoride and with hydrogen which is introduced into said zone via line 14. The isomerization conditions employed are such that the catalyst is maintained substantially in the liquid phase.

During the isomerization reaction, there is formed, within isomerization zone 12, a hydrocarbon phase 16 and a catalyst phase 18 separated from each other by an interface 20. At least a portion of the catalyst will be deactivated due to the formation of stable allylic and/or alkylaromatic carbonium ions of the formula $R^+TaF_6^-$ wherein R is an allyl or alkylaromatic compound.

Although not necessary to the practice of the present invention, it may be desirable for economic reasons to separate at least a portion of the deactivated or partially deactivated catalyst from the hydrocarbon phase prior to regeneration. Preferably, substantially all of the hydrocarbon phase, i.e., all but that portion dissolved or otherwise entrained in the catalyst, is separated from the catalyst prior to regeneration. The separation may be accomplished by any suitable means (not shown) including settling and decanting, volatilization and the like.

As shown in the FIGURE, at least a portion of the catalyst phase is then passed via line 22 into regeneration zone 24 which contains a fixed bed 26 of palladium on a carbon support. Molecular hydrogen, i.e., hydrogen gas, is introduced into regeneration zone 24 via line 28 and intimately admixed with the substantially liquid acid catalyst phase present therein. During regeneration, alkyl and/or alkylaromatic carbonium ions are hydrogenated to give paraffins and/or naphthenes having the corresponding carbon number. Such compounds do not have an adverse affect on the acidity of the isomerization catalyst system and, thus, may be returned to isomerization zone 12 via line 30. The paraffins and/or naphthenes are then passed from isomerization zone 12 with the isomerate via line 32, said isomerate having a higher octane than the hydrocarbon feedstock. If desired, however, the paraffins and naphthenes could be extracted from the regenerated catalyst by techniques available to one skilled in the art and, thus, not be returned to the isomerization zone.

Also, during regeneration, the tantalum pentafluoride is separated from the stable complex and enters the liquid phase. As such, the solubility of tantalum pentafluoride in hydrogen fluoride may be exceeded, thereby resulting in the formation of a precipitate of tantalum pentafluoride. Thus, it may be desirable to introduce hydrogen fluoride into regeneration zone 24 via line 34 to prevent precipitation of the tantalum pentafluoride.

Use of the present regeneration process has the advantage of providing a simple and convenient means to regenerate all or only a portion of the deactivated or partially deactivated hydrocarbon conversion catalyst. In addition, since the regeneration is effected under relatively mild conditions, the production of gases (e.g. $C_1$-$C_4$ hydrocarbons) via cracking is substantially eliminated. Further, the paraffinic and naphthenic hydrocarbons formed during regeneration can be returned to they hydrocarbon conversion process without any deleterious affect on said process.

The following examples are presented to further illustrate the regeneration process of the present invention and are not intended to unduly restrict the limits of the claims appended hereto.

EXAMPLE 1 — REGENERATION OF SUBSTANTIALLY DEACTIVATED CATALYST

After the isomerization of a fresh catalyst (44.5 g. HF, 55.2 g. $TaF_5$, 90 ml $nC_6$, 10 ml $CyC_6$, 90–120 psig pressure maintained with $H_2$, 50 ± 2° C) had been established in a 300 cc Hastelloy C stirred autoclave (Table I, Run No. I, columns 1 and 2), the catalyst was deactivated by removing the hydrogen and stirring at 70° C for 1 hour. The catalyst was found to be substantially inactive (Table I, Run No. II, columns 3, and 4). All but approximately 45 ml of they hydrocarbon layer was removed, 5.0 g. of a catalyst containing 5 wt. % Pd. on carbon was added and the autoclave was pressured to 1,000 psig with hydrogen and heated to 50° C. After 20 hours, hydrogen consumption was 476 psig (~0.16 mole $H_2$). Fresh hydrocarbon feed was added to the autoclave. The activity of the acid was no such as to produce 16.91% 2, 2 $DMC_4$ after 1 hour (Table I, Run No. III, columns 5 and 6). The mixture was pressured to 1000 psig with hydrogen and allowed to stir for another 44 hours at 50° C. Hydrogen consumption was 565 psig. After washing and replenishing with fresh feed (Table I, Run No. IV, columns 7 and 8), activity of the mixture was such as to product 23.16% 2, 2 $DMC_4$ after 1 hour. The mixture was discarded. The complete results of this experiment are shown in Table I below.

TABLE I

| Run No. | Active[a] I | | Deactivated[b] II | | 1st Reactivation[b] III | | 2nd Reactivation[b] IV | |
|---|---|---|---|---|---|---|---|---|
| Column No. | 1 | 2 | 3 | 4 | 5 | 6 | 7 | 8 |
| Time of sample, hr. | 0 | 1 | 0 | 1 | 0 | 1 | 0 | 1 |
| Air $C_1$, $CO_2$ | 0.21 | 0.18 | 0.20 | 0.23 | 0.46 | 0.62 | 0.13 | 0.31 |
| $C_2$ | 0.03 | 0.49 | 0.17 | 0.03 | 0.12 | 0.13 | 0.84 | 0.59 |
| $C_3$ | 0.03 | 0.29 | 0.25 | 0.26 | 0.08 | 0.14 | 0.05 | 0.12 |
| $iC_4$ | 0.01 | 0.57 | 0.33 | 0.37 | 0.37 | 0.43 | 0.05 | 0.12 |
| $nC_4$ | 0.02 | 0.21 | 0.07 | 0.07 | trace | 0.07 | 0.04 | 0.09 |
| $iC_5$ | — | 0.44 | 0.12 | 0.10 | 0.12 | 0.12 | 0.08 | 0.12 |
| $nC_5$ | — | 0.08 | — | — | — | trace | trace | trace |
| 2, 2 $DMC_4$ | 2.64 | 40.93 | 0.15 | 0.73 | 0.36 | 16.91 | 2.06 | 23.16 |
| 2, 3 $DMC_4$, 2 $MC_5$ | 18.61 | 30.71 | 3.48 | 11.89 | 3.45 | 36.66 | 3.23 | 35.41 |
| $3MC_5$ | 6.80 | 10.77 | 2.20 | 4.21 | 1.87 | 13.06 | 3.30 | 12.50 |
| $nC_6$ | 54.36 | 6.72 | 74.77 | 63.96 | 75.16 | 15.16 | 72.45 | 11.32 |
| MCP | 2.75 | 1.39 | 5.71 | 2.42 | 6.27 | 3.21 | 7.40 | 3.19 |
| $CyC_6$ | 14.62 | 6.65 | 12.54 | 15.55 | 11.67 | 13.38 | 10.35 | 13.06 |
| $C_7$–$C_8$ | — | 0.53 | — | 0.17 | 0.06 | 0.09 | — | — |

[a]determined for 100 ml 90/10
[b]determined for exactly the same volume of feed (145 ml)

The 23.16% 2, 2 $DMC_4$ corresponds to approximately 65% reactivation. This is based on a separate experiment wherein 5.0 g. of 5 wt. % Pd./C on carbon catalyst added to a fresh $TaF_5$/HF catalyst produced 35.88% 2, 2 $DMC_4$ after one hour.

EXAMPLE 2 —REGENERATION OF PARTIALLY DEACTIVATED CATALYST

The experiment similar to Example 1 was repeated. The activity of a fresh catalyst (43.0 g. HF, 55.2 g. $TaF_5$, approximately 145 ml of feed in volume ratio of 88 ml $nC_6$: 10 ml $CyC_6$: 2 ml $C_6H_6$, 125 psig pressure maintained by $H_2$, 50 ± 2° C) was found to produce 29.47% 2, 2 $DMC_4$ after 0.50 hour (Table II, Run No. I, columns 1, 2 and 3). The catalyst was then partially deactivated (50°–60° C with little or no hydrogen) to the extent that it only produced 10.10% 2, 2 $DMC_4$ after 0.50 hour (Table II, Run No. II, columns 4, 5 and 6). All but approximately 45 ml of the hydrocarbon layer was removed, 1.0 g. 5% Pd./C was added, and the autoclave was pressured up to 200 psig with hydrogen and stirred at 55° C. As hydrogen was consumed, it was replenished. After approximately 3.5 hours, hydrogen consumption had almost stopped. Fresh hydrocarbon feed was then added to the autoclave. The activity of the acid was now such as to produce 28.23% 2, 2 $DMC_4$ after 0.50 hours (Table II, Run No. III, columns 7, 8 and 9). This corresponds to approximately 100% reactivation based upon the activity of the fresh catalyst. The complete results of this experiment are shown in Table II below.

TABLE II[a]

| | Active I | | | Partially Deactivated II | | | Reactivated III | | |
|---|---|---|---|---|---|---|---|---|---|
| Column No. | 1 | 2 | 3 | 4 | 5 | 6 | 7 | 8 | 9 |
| Time of Sample, hr. | 0 | ½ | 1 | 0 | ½ | 1 | 0 | ½ | 1 |
| Air, $C_1$, $CO_2$ | 0.13 | 0.19 | 0.21 | 0.12 | 0.27 | 0.13 | 0.16 | 0.34 | 0.46 |
| $C_2$ | 0.37 | 0.18 | 0.06 | 0.15 | 0.01 | 0.10 | 0.09 | 0.06 | — |
| $C_3$ | — | 0.10 | 0.18 | — | 0.03 | 0.04 | 0.03 | 0.09 | 0.15 |
| $iC_4$ | — | 0.20 | 0.56 | 0.05 | 0.19 | 0.30 | 0.16 | 0.30 | 0.47 |
| $nC_4$ | — | 0.08 | 0.15 | trace | 0.02 | 0.03 | 0.02 | 0.06 | 0.09 |
| $iC_5$ | — | 0.09 | 0.24 | trace | — | 0.05 | 0.04 | 0.11 | 0.19 |
| $nC_5$ | — | trace | 0.04 | trace | — | — | — | — | 0.02 |
| 2, 2 $DMC_4$ | 0.19 | 29.47 | 39.94 | 0.81 | 10.10 | 17.98 | 1.00 | 28.23 | 37.20 |
| 2, 3 $DMC_4$, $2MC_5$ | 2.73 | 26.98 | 29.53 | 5.15 | 33.37 | 35.37 | 7.07 | 30.46 | 28.85 |
| $3MC_5$ | 2.91 | 9.42 | 10.25 | 2.94 | 11.85 | 12.52 | 2.54 | 10.67 | 10.04 |
| $nC_6$ | 73.73 | 16.73 | 5.69 | 70.16 | 24.22 | 13.56 | 68.99 | 10.83 | 5.66 |
| MCP | 6.91 | 3.10 | 2.20 | 5.46 | 3.30 | 3.22 | 3.08 | 3.46 | 3.41 |
| $C_6H_6$ | 1.65 | 1.13 | 0.72 | 2.27 | 2.12 | 2.05 | 1.56 | trace | — |
| $CyC_6$ | 11.38 | 12.41 | 10.02 | 12.88 | 14.45 | 14.42 | 15.13 | 15.08 | 13.32 |
| $C_7$–$C_9$ | — | 0.16 | 0.17 | trace | trace | 0.20 | 0.12 | 0.31 | 0.31 |

[a]Exactly the same quantities of feed (145 ml) were used in each activity test.

What is claimed is:

1. In a hydrocarbon conversion process which comprises contacting a hydrocarbon feedstock with a substantially liquid phase acid catalyst comprising (a) a metal halide selected from the group consisting of the fluorides, chlorides and bromides of tantalum, niobium, antimony and boron and the chlorides and bromides of aluminum and gallium and (b) a Bronsted acid containing fluoride, thereby forming a hydrocarbon phase and a catalyst phase, said catalyst phase having become at least partially deactivated due to the presence of a compound selected from the group consisting of allylic carbonium ions, alkylaromatic carbonium ions and mixtures thereof in said acid catalyst, the improvement which comprises regenerating at least a portion of said catalyst by contact with a noble metal selected from the group consisting of platinum, palladium, iridium, ruthenium, rhodium and mixtures thereof and hydrogen at a temperature in the range of from 0° to about 150° C. for a period of time sufficient to obtain an acid catalyst possessing a greater activity for hydrocarbon conversion than that possessed by said deactivated catalyst.

2. The process of claim 1 wherein said acid catalyst comprises a metal halide selected from the group consisting of the fluorides, chlorides and bromides of tantalum, niobium and boron in combination with a Bronsted acid selected from the group consisting of hydrogen fluoride, fluorosulfonic acid, trifluoromethanesulfonic acid and mixtures thereof.

3. The process of claim 2 wherein the Bronsted acid is hydrogen fluoride.

4. The process of claim 1 wherein the amount of hydrogen present during regeneration is sufficient to maintain a hydrogen partial pressure of at least 5 psig.

5. The process of claim 1 wherein the hydrogen is substantially dispersed in the partially deactivated catalyst during regeneration.

6. The process of claim 1 wherein the noble metal is supported on a solid carrier that is substantially inert to the partially deactivated acid catalyst.

7. The process of claim 1 wherein at least a portion of the acid catalyst thus regenerated is recycled to the hydrocarbon conversion process.

8. The process of claim 1 wherein said acid catalyst comprises a metal halide selected from the group consisting of tantalum pentafluoride, niobium pentafluoride and mixtures thereof and hydrogen fluoride.

9. In a hydrocarbon conversion process which comprises contacting a hydrocarbon feedstock with a substantially liquid phase acid catalyst comprising (a) a metal halide selected from the group consisting of tantalum pentafluoride, niobium pentafluoride and mixtures thereof and hydrogen fluoride, thereby forming a hydrocarbon phase and a catalyst phase, said catalyst phase having become at least partially deactivated due to the presence of a compound selected from the group consisting of allylic carbonium ions, alkylaromatic carbonium ions and mixtures thereof in said acid catalyst, the improvement which comprises regenerating at least a portion of said catalyst by contact with a noble metal selected from the group consisting of platinum, palladium, and mixtures thereof and hydrogen, said regeneration being effected at a temperature in the range of from 0° to about 150° C. and at a hydrogen partial pressure of at least 5 psig for a period of time sufficient to obtain an acid catalyst possessing a greater activity for hydrocarbon conversion than that possessed by said deactivated catalyst.

10. The process of claim 9 wherein the noble metal is palladium.

11. The process of claim 9 wherein the temperature during regeneration ranges from about 0° to about 100° C.

12. The process of claim 9 wherein the hydrogen is substantially dispersed in the partially deactivated catalyst during regeneration.

13. The process of claim 9 wherein the noble metal is supported on a solid carrier that is substantially inert to the partially deactivated acid catalyst.

14. The process of claim 13 wherein the support is carbon.

15. The process of claim 9 wherein said hydrocarbon conversion process is isomerization and said hydrocarbon feedstock comprises an acyclic hydrocarbon having at least four carbon atoms, an alicyclic hydrocarbon having at least six carbon atoms and mixtures thereof.

16. The process of claim 9 wherein said hydrocarbon conversion process is alkylation and said hydrocarbon feedstock comprises a component selected from the group consisting of an acyclic hydrocarbon having at least one carbon atom, an alicyclic hydrocarbon having at least 5 carbon atoms, an aromatic and alkyl aromatic hydrocarbon having at least 6 carbon atoms and mixtures thereof, and said hydrocarbon feedstock is reacted with an olefin containing from 2 to about 12 carbon atoms per molecule.

17. In an isomerization process which comprises contacting a feedstock containing a component selected from the group consisting of acyclic hydrocarbons having at least four carbon atoms, alicyclic hydrocarbons having at least six carbon atoms and mixtures thereof with an acid catalyst comprising a metal fluoride selected from the group consisting of tantalum pentafluoride, niobium pentafluoride and mixtures thereof in combination with hydrogen fluoride, thereby forming a hydrocarbon phase and a catalyst phase, said catalyst phase having become at least partially deactivated due to the presence of a compound selected from the group consisting of allylic carbonium ions, alkylaromatic carbonium ions and mixtures thereof in said acid catalyst, the improvement which comprises regenerating at least a portion of said catalyst in a regeneration zone by contact therein with a noble metal selected from the group consisting of platinum, palladium and mixtures thereof and hydrogen, said regeneration being effected at a temperature in the range of from about 0° to about 150° C. and at a hydrogen partial pressure in the range of from about 5 to about 2000 psig for a period of time sufficient to obtain a catalyst possessing a greater activity for isomerization than that possessed by said deactivated catalyst.

18. The process of claim 17 wherein the noble metal is supported on a solid carrier that is substantially inert to the acid catalyst.

19. The process of claim 18 wherein the noble metal is palladium.

20. The process of claim 18 wherein the support is carbon.

21. The process of claim 17 wherein the temperature ranges from about 25° to about 75° C.

22. In an alkylation process which comprises contacting a feedstock containing a component selected from the group consisting of acyclic hydrocarbons having at least one carbon atom, alicyclic hydrocarbons having at least 5 carbon atoms, aromatic and alkyl aromatic hydrocarbons having at least 6 carbon atoms and mixtures thereof, with an olefin containing from 2 to about 12 carbon atoms per molecule and with an acid catalyst comprising a metal fluoride selected from the group consisting of tantalum pentafluoride, niobium pentafluoride and mixtures thereof in combination with hydrogen fluoride, thereby forming a hydrocarbon phase and a catalyst phase, said catalyst having become at least partially deactivated due to the presence of a compound selected from the group consisting of allylic carbonium ions, alkylaromatic carbonium ions and mixtures thereof in said acid catalyst, the improvement which comprises regenerating at least a portion of said catalyst in a regeneration zone by contact therein with a noble metal selected from the group consisting of platinum, palladium and mixtures thereof and hydrogen, said regeneration being effected at a temperature in the range of from about 0° to about 150° C. and at a hydrogen partial pressure in the range of from about 5 to about 2000 psig for a period of time sufficient to obtain a catalyst possessing a greater activity for alkylation than that possessed by said deactivated catalyst.

23. The process of claim 22 wherein the noble metal is supported on a solid carrier that is substantially inert to the acid catalyst.

24. The process of claim 23 wherein the noble metal is palladium.

25. The process of claim 23 wherein the support is carbon.

26. The process of claim 22 wherein the temperature ranges from about 25° to about 75° C.

* * * * *